(12) United States Patent
Sandin et al.

(10) Patent No.: US 7,789,985 B2
(45) Date of Patent: Sep. 7, 2010

(54) METHOD FOR PRODUCING DIAPER PANTS OF THE DISPOSABLE TYPE

(75) Inventors: Cécile Sandin, Molndal (SE); Kenneth Strannemalm, Floda (SE); Kent Hermansson, Vastra Frolunda (SE); Hans Een, Molnlycke (SE)

(73) Assignee: SCA Hygiene Products AB, Goteborg (SE)

( * ) Notice: Subject to any disclaimer, the term of this patent is extended or adjusted under 35 U.S.C. 154(b) by 735 days.

(21) Appl. No.: 11/582,385

(22) Filed: Oct. 18, 2006

(65) Prior Publication Data

US 2007/0034315 A1 Feb. 15, 2007

Related U.S. Application Data

(62) Division of application No. 10/753,404, filed on Jan. 9, 2004, now abandoned.

(60) Provisional application No. 60/438,999, filed on Jan. 10, 2003.

(51) Int. Cl.
*A61F 13/15* (2006.01)

(52) U.S. Cl. .................... 156/73.1; 156/226; 156/308.2

(58) Field of Classification Search ........................ None
See application file for complete search history.

(56) References Cited

U.S. PATENT DOCUMENTS

| | | | |
|---|---|---|---|
| 3,604,015 A | 9/1971 | Dove | |
| 3,773,002 A * | 11/1973 | Burton | 112/470.05 |
| 4,205,679 A | 6/1980 | Repke et al. | |
| 4,747,846 A | 5/1988 | Boland et al. | |
| 5,074,854 A | 12/1991 | Davis | |
| 5,091,038 A * | 2/1992 | Greller et al. | 156/443 |
| 5,236,430 A | 8/1993 | Bridges | |
| 5,246,433 A | 9/1993 | Hasse et al. | |

(Continued)

FOREIGN PATENT DOCUMENTS

EP 0187728 A2 7/1986

(Continued)

OTHER PUBLICATIONS

English Translation of Notice of Reasons for Rejection in corresponding Application No. JP 2006-500741 dated Jun. 2, 2009.

*Primary Examiner*—Richard Crispino
*Assistant Examiner*—Barbara J. Musser
(74) *Attorney, Agent, or Firm*—Buchanan Ingersoll & Rooney PC

(57) ABSTRACT

A method to produce an absorbent article using a blank, includes the following steps: folding the side-edge portions of the side parts of either the rear portion or front portion in towards the inner cover sheet over supports placed on the side parts of this portion and extending along the full length of this portion, folding the blank about a transverse line in the crotch portion so that the end edges of the front portion and rear portion come to lie edge-to-edge and so that the side-edge portions of the folded-in portion overlap the folded-in side-edge portions of the second portion; and welding together the overlapping side-edge portions of the side parts within the area of the supports by way of ultrasonic or thermal welding.

10 Claims, 3 Drawing Sheets

U.S. PATENT DOCUMENTS

| | | | |
|---|---|---|---|
| 5,569,234 A * | 10/1996 | Buell et al. ................. 604/396 |
| 5,607,537 A | 3/1997 | Johnson et al. |
| 6,042,673 A | 3/2000 | Johnson et al. |
| 6,149,637 A | 11/2000 | Allen et al. |
| 6,394,991 B1 | 5/2002 | Takei et al. |
| 6,447,628 B1 * | 9/2002 | Couillard et al. ............ 156/204 |
| 6,461,344 B1 * | 10/2002 | Widlund et al. ............. 604/390 |
| 2003/0120252 A1 | 6/2003 | Franke et al. |
| 2003/0120254 A1 | 6/2003 | Franke et al. |

FOREIGN PATENT DOCUMENTS

| | | |
|---|---|---|
| EP | 0755238 B1 | 8/1999 |
| GB | 2267024 | 11/1993 |
| JP | 3021190 | 1/1991 |
| JP | 07-75653 | 3/1995 |
| JP | 11-513295 | 11/1999 |
| JP | 2002-505159 | 2/2002 |
| WO | WO 97/13485 | 4/1997 |
| WO | 99/44559 | 9/1999 |

* cited by examiner

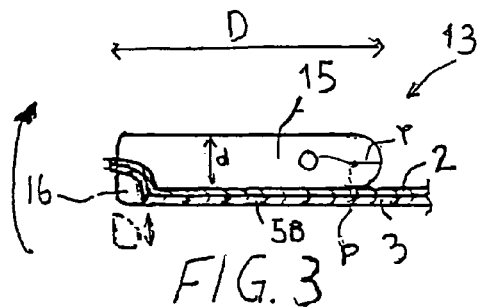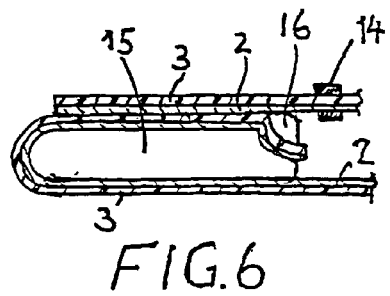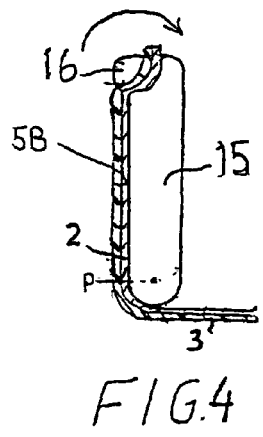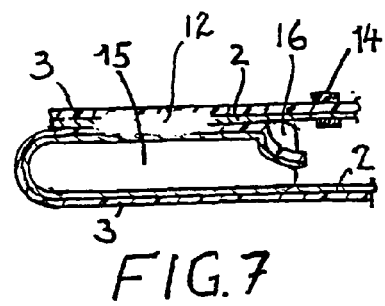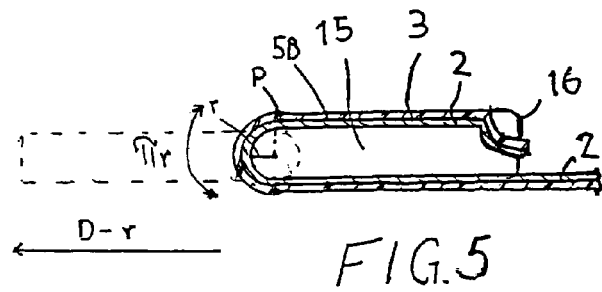

METHOD FOR PRODUCING DIAPER PANTS OF THE DISPOSABLE TYPE

CROSS-REFERENCE TO RELATED APPLICATIONS

The present application is a division of copending application Ser. No. 10/753,404 filed Jan. 9, 2004, which claims the benefit under 35 U.S.C. §119(e) of provisional application No. 60/438,999 filed on Jan. 10, 2003, the entire contents of which are incorporated by reference.

BACKGROUND

1. Technical Field

The present invention relates to a method using a blank for an absorbent article in the form of diaper pants or a sanitary panty in order to produce such an article, which blank includes an absorbent body enclosed between an inner, liquid-permeable cover sheet and an outer cover sheet, at least one cover sheet being made of a material which can be thermally welded, which blank further has a front portion, a rear portion, and a crotch portion which extends between these portions and includes and is delimited by the leg openings of the blank, said front portion and rear portion having side parts which extend laterally outside the absorbent body from the waist band to the leg openings. The invention also relates to an article of the disposable type produced by means of this method.

2. Related Art

Diaper pants are an alternative to open type diapers and have become increasingly popular for slightly older infants. Today's diaper pants have a good fit, which contributes to ensuring that they function well and which in addition gives them an aesthetically attractive look. Unlike conventional open diapers which look like pants once they have been fitted on the user, diaper pants look like pants right from the start, because the manufacturer has joined the side-edge portions of the front and rear portions of the diaper together. Diaper pants are easy to change with the user standing, by pulling them down just like underpants and then putting on a new set of diaper pants. U.S. Pat. No. 3,604,015 discloses diaper pants in which a blank with front and rear portions of the same width is folded about a transverse line in the crotch portion, after which the edge portions of the folded blank which have been laid on one another are sewn together. Such a connection between the side-edge portions protrudes like a flange from the diaper pants and detracts from their appearance. To improve the appearance, these known diaper pants are produced by a method in which, in a final stage, the blank for the diaper pants is turned inside out so that said flange is situated on the inside of the diaper pants and does not therefore spoil the appearance of the diaper pants. A disadvantage of such a flange connection is that it is exposed to forces (peel forces) directed at right angles to the connected surfaces and for this reason it must be very strong.

WO 99/44559 and U.S. Pat. No. 5,607,537 disclose methods of producing flangeless seams and thereby avoiding peel forces. However, these seams comprise many material layers and are therefore bulky.

It is difficult to pull the diaper pants off when the user is lying down. If the diaper pants contain excrement, it is virtually impossible to pull the diaper pants off without soiling the user or his/her clothes. To solve this problem, it is known to design diaper pants such that they can be opened along the sides in the same way as conventional open diapers. For example, from EP-B1-0 755 238 it is known to connect the side-edge portions of the front and rear portions with the aid of detachable and resealable fastenings. From GB-A-2 267 024 it is known to arrange weakening lines in the side portions of the diaper pants in order to allow the diaper pants to be opened, and the diaper pants in EP-A2-0 187 728 have side seams which can be torn open.

SUMMARY

The present invention concerns in the first instance a method for producing diaper pants which ensures an aesthetically pleasing connection between the side-edge portions of the front and rear portions of the diaper pants without any step of turning the blank inside out, and which connection is designed such that the forces exerted on the diaper pants are largely taken up as shearing forces, and which method makes use of the fact that the cover sheets included in the diaper pants can be welded using heat. Secondly, the invention relates to a method by which it is possible to obtain a connection between the side-edge portions of the front and rear portions which reliably withstands the forces to which the diaper pants are exposed during normal use and handling, but which can nevertheless be easily torn open by an adult.

These objects are achieved by means of a method using a blank for an absorbent article in the form of diaper pants or a sanitary panty in order to produce such an article, which blank includes an absorbent body enclosed between an inner, liquid-permeable cover sheet and an outer cover sheet, at least one cover sheet being made of a material which can be thermally welded, which blank further has a front portion, a rear portion, and a crotch portion which extends between these portions and includes and is delimited by the leg openings of the blank, said front portion and rear portion having side parts which extend laterally outside the absorbent body from the waist band to the leg openings, characterized by the following steps: side-edge portions of the side parts of either the rear portion or front portion are folded in towards the inner cover sheet over supports which have been placed on the side parts of this portion;

and which extend along the full length of this portion, after which the blank is folded about a transverse line in the crotch portion so that the end edges of the front portion and rear portion, forming the waist band of the finished article, come to lie edge-to-edge and so that the side-edge portions of the folded-in portion overlap the folded-in side-edge portions of the second portion;

and thereafter the overlapping side-edge portions of the side parts are welded together within the area of the supports by means of ultrasonic or thermal welding. Because the side-edge portions are connected overlapping one another, an aesthetically pleasing weld seam is obtained without turning the blank inside out, which weld seam is exposed only to shear forces and can thus be made to be tearable. Furthermore, the side-edge portions only overlap one another singly, which means that the portions joined together are not bulky.

According to one embodiment, the supports are placed on the side parts before the side-edge portions of the side parts of the rear portion or front portion are folded in, and this folding is obtained by turning the supports. Furthermore, in one embodiment, the front portion and rear portion of the blank are given the same width in the initial state and the side-edge portions of the side parts of the portion of the front portion and rear portion which are to have unfolded side-edge portions are offset sideways towards each other by a distance which corresponds to the reduction in width as a result of the folding-in of the side-edge portions of the second portion before folding the blank about a transverse line in the crotch portion. At least those parts of the side-edge portions of the side parts of the portion of front portion and rear portion which is to have unfolded side edge portions and extends within the areas of the supports are kept in a relaxed and unstressed state during the folding and welding steps.

In an alternative embodiment, the portion of front portion and rear portion which is to have unfolded side edge portions is given a width corresponding to the width of the second portion after its side-edge portions have been folded in across the supports.

One embodiment of the invention also relates to an absorbent article in the form of diaper pants including an absorbent body enclosed between an inner, liquid-permeable cover sheet and an outer cover sheet, at least one of said cover sheets being made of a material that can be thermally welded, which article further has a front portion, a rear portion, and a crotch portion which extends between these portions and which includes and is delimited by the leg openings of the blank, the front portion and rear portion having side parts which extend laterally outside the absorbent body from the waist opening to the leg openings and which are at least partially elastic, characterized in that the side-edge portions of the front portion and of the rear portion overlap the side-edge portions of the second portion of these portions without comprising folded parts and are connected to these side-edge portions by means of a weld seam which extends along the full length of the side-edge portions.

In one embodiment, the weld seam has a width of 6-10 mm, preferably 7-9 mm, and most preferably 8 mm, and it can be torn open. The weld seam preferably has a strength of 10-45 N/25 mm.

BRIEF DESCRIPTION OF THE DRAWINGS

The invention will now be described with reference to the attached figures:

FIGS. 3-5 show diagrammatic cross sections of an edge portion of a blank for diaper pants during application of a weld support according to a first embodiment of the method according to the invention, FIG. 6 shows a diagrammatic cross section of edge portions of the front and rear portions of the diaper pants blank which have been folded together before the welding operation has been performed, FIG. 7 shows a view similar to FIG. 6 after the welding operation has been performed.

DETAILED DESCRIPTION OF THE PREFERRED EMBODIMENTS

Figure 1:
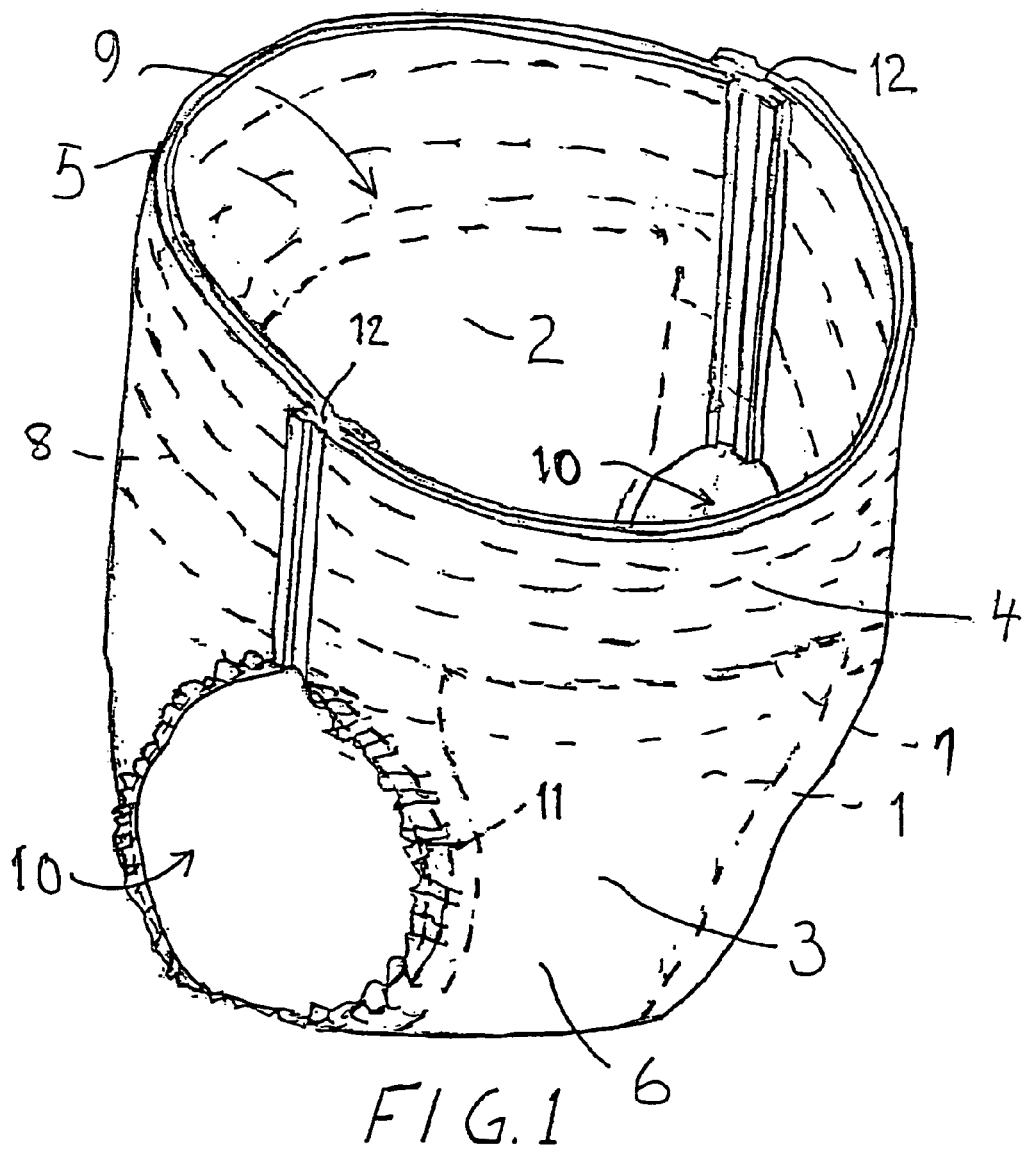
FIG. 1 shows a diagrammatic perspective view of diaper pants according to one embodiment of the invention.

A preferred embodiment of diaper pants according to the invention is shown in FIG. 1. The diaper pants comprise an absorbent body 1 enclosed between an inner, liquid-permeable cover sheet 2 and an outer liquid-tight cover sheet 3. The cover sheets 2 and 3 are of identical shape and extend outside the absorbent body 1 around its entire circumference. In the parts lying outside the absorbent body 1, the cover sheets 2, 3 are connected to each other, for example by welding or gluing. The diaper pants have a front portion 4, a rear portion 5, and a crotch portion 6 lying between these portions.

In one embodiment, the cover sheets are elastic, at least at the waist band and in the side panels of the front and rear portions 4, 5 lying laterally outside the absorbent body 1. In the embodiment shown, the elasticity of the cover sheets has been obtained by elastic threads 7, 8, which in a stretched state having been arranged between the cover sheets and secured to these by welding or gluing. The elasticity can also be obtained in other ways, for example by one or both of the cover sheets being made of elastic material. If both cover sheets are made of elastic material, one of the sheets does not need to be arranged in the stretched state, which maybe necessary if only one of the sheets is elastic. It is also possible for the side panels of the front and rear portions 4, 5 lying laterally outside the absorbent body 1 to consist of separate panels made of elastic material, while the waist band is made elastic by arranging stretched elastic threads or bands between the cover sheets 2, 3.

In one embodiment, the diaper pants are shaped like pants with a waist opening 9 and two leg openings 10. Leg elastic in the form of stretched elastic threads 11 are arranged around the leg openings 10.

The mutually facing side-edge portions of the front and rear portions 4, 5 of one embodiment of the diaper pants overlap one another and are connected to one another by means of weld seams 12 which may be generated by ultrasonic welding or thermal welding. The weld seams may have a width of 6-10 mm, preferably 7-9 mm, and most preferably 8 mm, and a strength of 10-45 N/25 mm measured in the manner set out below. Such a seam is able, with good margins, to cope with all normally occurring loads which arise during normal use of the diaper pants, but can still be easily torn open by an adult. In this way, the diaper pants can be removed from a user lying down, in the same way as an open diaper, which means that diaper pants containing excrement can be changed with minimal risk of soiling of the user's clothes.

Figure 10:
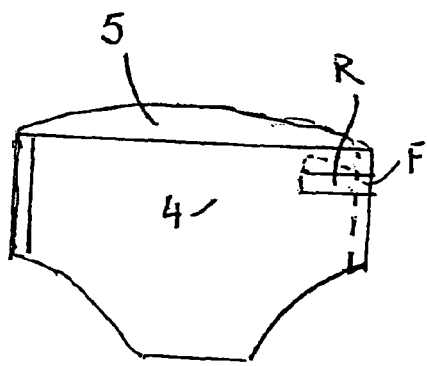
FIGS. 10 and 11 illustrate a method of measuring the weld strength.
Figure 11:
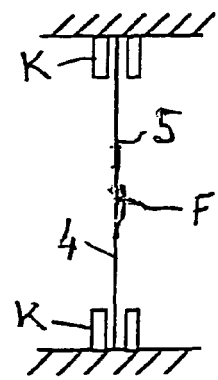

The seam strength may be measured in the following way. First, in the manner illustrated in FIG. 10, a strip R with a width of 25 mm is cut out from the front 4 and rear 5 side parts of diaper pants, which side parts are connected to one another by a seam F. The ends of this strip R are then clamped securely in the clamps K of a stress gauge, which clamps have a width of 25 mm. The clamps are then moved from one another at a speed of 300 mm/min and the force upon rupture of the seam or strip is recorded.

The liquid-permeable cover sheet 2 consists, for example, of a nonwoven, e.g., a spunbond nonwoven, a carded nonwoven, a meltblown nonwoven or a nonwoven laminate, e.g., a spunbond-meltblown-spunbond (SMS) laminate. The fibers used to build up the nonwoven material can consist of fibres of polyolefins, for example, polyethylene or polypropylene, or of polyester. The nonwoven material can further consist of a mixture of several different types of fibers or of fibres which consist of several different polymers, called copolymers. Other materials which are used for liquid-permeable cover sheets, the so-called top sheets, for absorbent articles such as nonwovens of synthetic and/or natural fibers, perforated plastic sheets or laminates of these materials, can of course also be used as cover sheet 2.

The outer cover sheet 3 may consist of a nonwoven or a material built up from several nonwoven sheets, for example an SMS material. It may also consist of a plastic sheet, preferably of the breathable type, or a laminate of a plastic sheet and a nonwoven. All materials used as the so-called reverse sheet for absorbent articles can be used.

To obtain the weld seams 12, it is sufficient for one of the cover sheets 2, 3 to be made of material that can be thermally welded. However, it is preferable for both cover sheets to be made of materials that can be thermally welded, preferably also of materials whose melt points are similar to one another. For this reason, both the cover sheets 2, 3 are preferably made of material containing fibers which can be completely or partially melted.

In one embodiment, the absorbent body 1 preferably comprises a sheet of cellulose fibers with or without admixture of superabsorbents and/or binder fibres. Other materials such as foamed material or moss may also be used separately or in combination with cellulose fibers. The absorbent body may also be built up from several sheets and advantageously comprises a sheet of material having a high permeability, for example a sheet of wadding. If the outer cover sheet 3 is not liquid-tight, the absorbent body comprises an impermeable sheet on its side facing the outer cover sheet.

If the side panels are made of elastic material, this may consist of elastomers produced from block copolymers, such as polyurethanes, copolyether esters, polyamide-polyether block copolymers, ethylene-vinylacetates (EVA) and the like, including polyurethanes available from E.I. Du Pont de Nemours Co., USA under the tradename LYCRA (also know as "spandex"); elastomeric styrene-butadiene copolymers, including those such as KRATON material available from Shell Chemical Company of Houston, Tex., USA; tetrablock copolymers including elastomeric styrene-poly(ethylene-propylene) block copolymers available from Shell Chemical Company of Houston, Tex., USA under the tradename KRATON; polyamides including polyether block amides available from Ato Chemical Company, USA under the tradename PEBAX; polyesters such as those available from E.I. Du Pont de Nemours Co. under the trade name HYTREL; single-site or metallocene-catalyzed polymers including single-site or metallocene-catalyzed polyolefins with a density of less than about 0.89 g/cm$^3$ from Dow Chemical Co., USA under the tradename AFFINITY; and natural and synthetic rubber.

An embodiment of a method for producing diaper pants according to FIG. 1 will now be described with reference to FIGS. 2-7. To simplify a comparison with the diaper pants in FIG. 1, components in FIGS. 2-7 have been given the same reference numbers as the corresponding components in the finished diaper pants in FIG. 1. For example, the web of liquid-permeable material in FIGS. 2-7 has been given the same reference number as the cover sheet 2 in the finished diaper pants.

Diaper pants according to the embodiment of FIG. 1 are produced in the following way.

Absorbent bodies 1 are laid on a running material web 3 of liquid-tight material, for example with the aid of a transfer wheel on which absorbent bodies 1 formed in a mat former wheel (not shown) have been placed. If the absorbent bodies 1 can be formed in synchrony with the advance of the material web 3, the transfer wheel can be omitted and the wheel can consist of a mat former wheel. The absorbent bodies 1 are deposited on the material web 3 in a row with the longitudinal direction of the bodies coinciding with the transverse direction of the web 3, i.e., at right angles to the direction of feed of the web 3 as is indicated by an arrow in FIG. 2. In the embodiment shown, the diaper pants are thus produced in what is called crosswise production. Before the absorbent bodies 1 have been deposited on the web 3, elastic threads 7, 8 and 11, forming the waist band, elastic side panels and leg elastic of the produced diaper pants, have been applied in the stretched state.

A material web 2 of liquid-permeable material is then placed on top of the row of absorbent bodies 1. The material web 2 can pass through a gluing unit immediately before application and is secured, with the aid of a pair of rollers, to the material web 3 in parts lying outside the absorbent bodies 1. If appropriate, the material web 2 is also secured to the rear side of each absorbent body 1. The elastic threads are expediently secured at the same time to the cover sheets, although it is of course possible to secure these to the material web 3 before the absorbent bodies have been applied. Instead of gluing, it is also possible to use ultrasonic or thermal welding to secure the cover sheets to each other and to secure the elastic threads or bands to one or both of the cover sheets 2, 3. A web of continuous diaper pants blanks is obtained by means of both cover sheets having been connected to one another. It should be noted that the production steps described thus far are conventional and well known to the skilled person.

Gripping and support members 13 are thereafter applied to the area which is to constitute the side-edge portions of the rear portion 5 of finished diaper pants, and gripping members 14 are arranged on the area which is to constitute the side-edge portions of the front portion 4 at a distance from the respective side edge of between 10 and 40 mm, preferably between 15 and 35 mm, and most preferably between 20 and 25 mm. Individual diaper pants blanks with leg openings 10 are then cut out from the web of continuous diaper pants blanks. The leg openings can of course be cut out before application of the gripping and support members 13.

Figure 2:
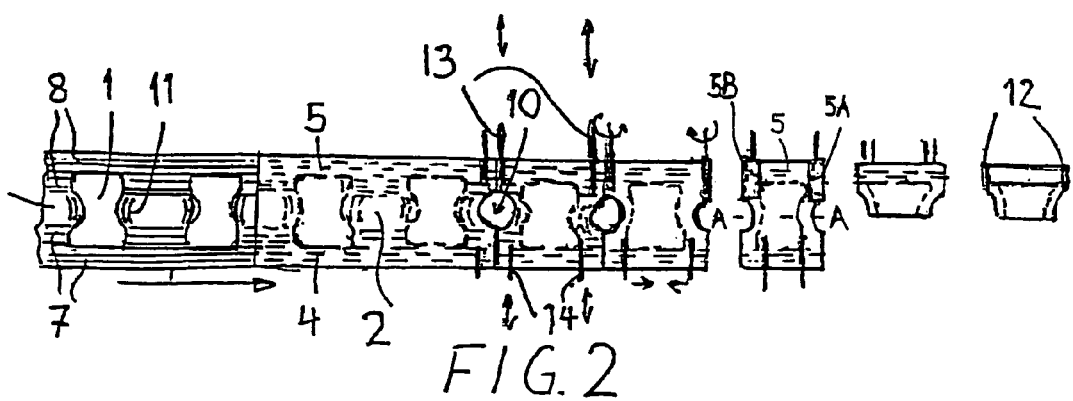
FIG. 2 shows a plan view illustrating diagrammatically a production line for producing diaper pants.

The side-edge portions 5A, 5B of the rear portion 5 of the diaper pants blank are then folded in across the inner liquid-permeable cover sheet 2 with the aid of the gripping and support members 13 so that the outer cover sheet 3 is facing the observer of FIG. 2 in these edge portions, and so that a support part 15 of the gripping and support member comes to lie between the folded-in part of the side-edge portion and the underlying part of the rear portion 5, This folding operation is described in more detail with reference to FIGS. 3-5, At the same time, the gripping and support members 14 are displaced symmetrically, in relation to the longitudinal axis of symmetry of the diaper pants blank, towards each other in the transverse direction of the diaper pants blank by a distance which corresponds to twice the width of the folded-in part of the side-edge portion of the rear portion.

FIGS. 3-5 show the folding-in of the side-edge portion SB of the rear portion 5 in greater detail. As can be seen from FIG. 3, the gripping and support member 13 is made up of two main parts, namely a support part 15 and a clamp part 16. The clamp part 16 is movable from the position shown by a broken line in FIG. 3 to come to bear against a recess in the support 15. The member 13 has a width D of 15-40 mm and a thickness d of 5-25 mm. In the embodiment shown, the members 13 are displaceable transversely with respect to the web of continuous diaper pants blanks, as is indicated by arrows in FIG. 2, and can also move in the direction of advance of the web. However, it is conceivable for the members 13 to be displaceable only in the direction of feed of the web. In such a case, however, one of the parts 15, 16 may be pivoted at right angles to the other part and to the plane shown in FIG. 2 to ensure that the members 13 can be applied to the web of continuous diaper pants blanks. After the members 13 have been applied to the web of continuous diaper pants blanks, the cover sheets are clamped securely between the parts 15 and 16. After the continuous web of diaper pants blanks has been separated in the transverse direction, the member 13 can begin to be turned about an axis O. In FIG. 4, the member 13 is shown when it has been turned through 90°, and in FIG. 5 when it has been turned through 180°. In FIG. 5, the broken lines show the position of the member 13 before turning. As can be seen from FIG. 5, the effect of the turning movement is that the outer edge of that side part of which the portion 5B forms a part has been displaced by the distance D-r in the direction towards the longitudinal axis of symmetry of the diaper pants blanks in relation to the position of this outer edge in the unfolded state of the side-edge portion 5B. r represents the distance between the rotation axis O and the nearest longitudinal edge of the member 13. In the embodiment shown, this edge has a semicircular shape. In FIGS. 3-5, a point P is shown at which the cover sheets 2, 3 are in contact with the member 13 both in the unfolded and in the folded state. During rotation of the member 13, this point P is displaced along the distance πr, i.e., the arc length of the semicircular edge. This means that if the member 13 is stationary during the rotation movement, the cover sheets 2, 3 may be stretched by a distance which corresponds to the arc length πr during the rotation movement of this member. This does not pose a problem if the side panels are made of elastic material, but in the present case when the elastic threads have been applied in the stretched state onto unfolded material webs, the member 13 may be moved sideways towards the longitudinal axis of symmetry of the diaper pants blank by a distance corresponding to the arc length before or during the rotation movement of the member 13. This distance may be added to the abovementioned displacement of the outer edge in order to obtain the distance by which the outer edge has approached the longitudinal axis of symmetry of the diaper pants blank. Rotation of the opposite side-edge portion 5A gives rise to a corresponding displacement of the outer edge of the opposite side part. The distance by which the gripping members 14 for the side-edge portions of the front portion are displaced towards one another corresponds expediently to the last-mentioned distance minus the shortening of these edge portions' outermost parts caused by the elastic threads 7 being allowed to contract from the stretched state to the relaxed state in those parts lying outside the gripping members 14. Relaxed state is intended to signify the state which these elastic threads assume when the diaper pants or the diaper pants blank are not subjected to external stresses.

The longitudinal edge of the member 13 lying nearest the rotation axis O can of course have a cross-sectional shape other than semicircular and thus have an arc length different than that shown in the embodiment.

When the displacements of the members 13, 14 and the rotation of the members 13 have been executed, the diaper pants blank is folded about a transverse line A-A in the crotch portion so that the end edges of the front and rear portions 4, 5, which form the waist band of the finished diaper pants, come to lie edge-to-edge and so that the parts of the side-edge portions of the front portion 4 lying outside the grip members 14 come to bear against the folded-in parts of the side-edge portions of the rear portion. Throughout the folding operation, the side-edge portions are held securely by the members 13, 14 which are thus entrained with the folding of the diaper pants blank. FIG. 6 shows a cross-sectional view of the edge portions of the front and rear portions 4, 5 of the diaper pants blank after the front portion 4 has been folded in across the rear portion 5. As can be seen from this figure, the gripping members 14 are situated inside the gripping and support members 13 as viewed in the sideways direction, which means that the side-edge portions are brought to bear against one another through the folding operation. The members 13, 14 are expediently arranged on a foldable frame which is either designed so that one half is foldable towards the other half, or so that the halves are folded against each other. In the latter case, the diaper pants blank, after folding, comes to lie in a plane at right angles to the plane in FIG. 2.

The folded-together diaper pants blank is then moved past ultrasonic horns or thermal welding jaws which generate weld seams 12. FIG. 7 shows the diaper pants directly after the side-edge portions have been welded together. The supports 15, which are preferably made of metal, e.g., iron, ensure that only the folded-in part of the side-edge portions of the rear portion 5 are secured to the side-edge portion of the front portion 4. The weld seams can consist of continuous seams or of patterns of spot welds or line welds.

After the welding has been carried out, the members 13, 14 are withdrawn from the finished diaper pants either by moving the members upwards in FIG. 2 or by pulling the diaper pants downwards from these members in FIG. 2. The diaper pants are then conveyed to a packaging station.

In the embodiment of the method according to the invention shown in FIG. 2, the welding is carried out intermittently, i.e. the diaper pants blank is held stationary during the welding operation. If instead the production line is to be completely continuous, the diaper pants blanks are preferably conveyed past stationary ultrasonic horns during displacement in the longitudinal direction. This can be done either by rotating the diaper pants blanks and the members gripping these, or by changing the direction of feed (change of conveyor belt). Another way is to use ultrasonic horns which are displaceable both in the direction of feed and in the transverse direction.

In the embodiment described, the web 2 of liquid-permeable material is placed on top of the web 3 of outer cover sheet material after absorbent bodies have been deposited thereon. It is of course possible for the webs to be changed around so that absorbent bodies are deposited on the web of liquid-permeable material, and the web of outer cover sheet material is applied last. The gripping and support members 13, 14 are in this case arranged on the underside of the web of diaper pants blanks, and the members 13 are rotated in opposite directions from those illustrated in FIG. 2.

Figure 8:
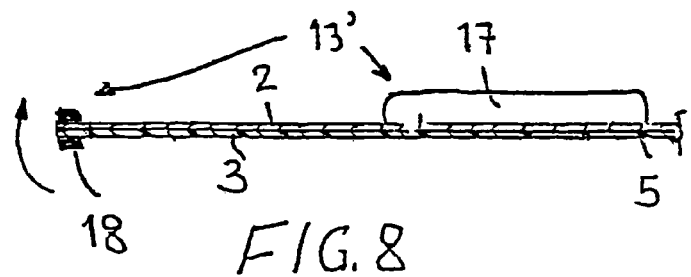
FIGS. 8 and 9 show diagrammatic cross sections of an edge portion of a diaper pants blank during application of a weld support according to a second embodiment of the method according to the invention.
Figure 9:
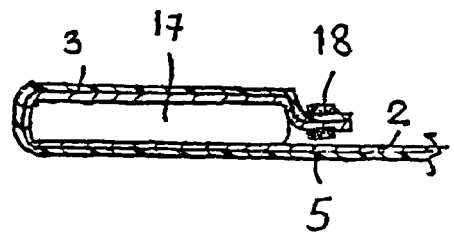

FIGS. 8 and 9 show an alternative embodiment of a gripping and support member 13'. This member differs from the member 13 in that the support part 17 is not rotatable and the gripping member 18 does not consist of a part integrated in the support part, but instead of a pivotable clamping fork 18. The folding-in of the side-edge portion of the rear portion 5 across the support 17 takes place exclusively by pivoting of the clamping fork 18 to the position shown in FIG. 9. It should be noted that the distance between the support part 17 and the clamping fork 18 is chosen so that the clamping fork 18 can be brought to bear against the cover sheet 2 of the rear portion 5, as is indicated in FIG. 9. This means that the side-edge portion of the front portion 4 can be brought to bear against the folded-in part of the rear portion 5 upon folding of the diaper pants blank about a transverse line in the crotch portion.

The described diaper pants can be designed for young children and also for incontinent adults.

The described embodiments can of course be modified within the scope of the invention. For example, the method can also be applied on production lines with so-called lengthways production, i.e., the diaper pants blanks have their longitudinal direction coincident with the direction of feed of the material webs, and the absorbent bodies can have another shape than the hourglass shape shown in the figures, e.g., rectangular. The supports 15 and 17 can be made of other materials, e.g., ceramic material, and the gripping members can be designed in a way other than that described. In the described embodiments, the front and rear portions of the diaper pants blanks are identical, but this is not necessary. For example, the side parts of the front or rear portion which are not to be folded could be given a smaller width than the side parts of the second portion. In such a configuration, the gripping members 14 do not have to be moved towards one another in order to ensure that the side-edge portions which are to be connected to each other will overlap after the diaper pants blank has been folded about a transverse fold line. To avoid waste, such a configuration should be used in crosswise production, the front portions of the diaper pants blanks being alternately located on different sides.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method to produce an absorbent article in the form of diaper pants, comprising:
   obtaining a blank comprising an absorbent body enclosed between an inner, liquid-permeable cover sheet and an outer cover sheet, at least one cover sheet being made of a thermally-weldable material; a front portion; a rear portion; and a crotch portion extending between the front and rear portions, wherein the crotch portion includes and is delimited by leg openings of the blank; wherein the front portion and rear portion have side parts extending laterally outside the absorbent body from a waist band to the leg openings;
   folding in side-edge portions of the side parts of one or both of the rear portion or front portion towards the inner cover sheet over respective supports placed in the side parts of either the rear or front portion and extending along the full length of the side-portions;
   folding the blank about a transverse line in the crotch portion so that the end edges of the front portion and rear portion come to lie edge-to-edge and so that the side-edge portions of the front or rear portion overlap the folded-in side-edge portions of the other of the front or rear portion;
   welding together the overlapping side-edge portions of the side parts within the area of the supports by means of ultrasonic or thermal welding,
   wherein the side-edge portions are secured to the respective supports via a clamp part that secures the side-edge portions between a surface of the respective supports and a surface of the clamp part.

2. The method according to claim 1, wherein the side-edge portions of the side parts of one of the rear portion or front portion are folded in towards the inner cover sheet over supports placed in the side parts of either the rear or front portion and extending along the full length of the side portions.

3. The method according to claim 1, wherein the supports are placed on the side parts before the side-edge portions of the side parts of the rear portion or front portion are folded in, and wherein folding is obtained by turning the supports.

4. The method according to claim 2, wherein the front portion and rear portion of the blank are the same width, and wherein the side-edge portions of the side parts of the portion of the front portion and rear portion with unfolded side edge portions are offset sideways towards each other by a distance which corresponds to the reduction in width as a result of the folding-in of the side-edge portions of the portion to be folded, before folding the blank about a transverse line in the crotch portion.

5. The method according to claim 4, wherein at least those parts extending within the areas for the supports of the side-edge portions of the side parts of the portion of the front portion and rear portion which is to have unfolded side-edge portions are kept in a relaxed and unstressed state during the folding and welding steps.

6. The method according to claim 2, wherein the portion of the front portion or rear portion with unfolded side edge portions has a width corresponding to the width of the other of the front or rear portion after its side-edge portions have been folded in over the supports.

7. The method according to claim 1, wherein the overlapping side-edge portions of the side parts of the one or both of the rear or front portion are welded together while the supports are in the side parts of the one or both of the rear or front portion.

8. The method according to claim 3, wherein the supports are provided on the inside of the fold created by the folding.

9. The method according to claim 1, wherein the supports are rigid.

10. A method to produce an absorbent article in the form of diaper pants, comprising:
    obtaining a blank comprising an absorbent body enclosed between an inner, liquid-permeable cover sheet and an outer cover sheet, at least one cover sheet being made of a thermally-weldable material; a front portion; a rear portion; and a crotch portion extending between the front and rear portions, wherein the crotch portion includes and is delimited by leg openings of the blank; wherein the front portion and rear portion have side parts extending laterally outside the absorbent body from a waist band to the leg openings;
    forming a fold by folding in side-edge portions of the side parts of one or both of the rear portion or front portion towards the inner cover sheet over respective supports placed in the side parts of either the rear or front portion and extending along the full length of the side-portions, the supports forming the fold via contact with the crease of the fold;
    folding the blank about a transverse line in the crotch portion so that the end edges of the front portion and rear portion come to lie edge-to-edge and so that the side-edge portions of the front or rear portion overlap the folded-in side-edge portions of the other of the front or rear portion;
    welding together the overlapping side-edge portions of the side parts within the area of the supports by means of ultrasonic or thermal welding,
    wherein the side-edge portions are secured to the respective supports via a clamp part that secures the side-edge portions between a surface of the respective supports and a surface of the clamp part.

* * * * *